(12) United States Patent
McKenzie et al.

(10) Patent No.: US 6,842,017 B2
(45) Date of Patent: Jan. 11, 2005

(54) FUEL CELL MIXTURE SENSOR

(75) Inventors: Isabelle McKenzie, Poquoson, VA (US); David Vanzuilen, Fremont, IN (US); Francois-Xavier Bernard, Corronsac (FR)

(73) Assignee: Siemens VDO Automotive Corporation, Auburn Hills, MI (US)

( * ) Notice: Subject to any disclaimer, the term of this patent is extended or adjusted under 35 U.S.C. 154(b) by 0 days.

(21) Appl. No.: 10/284,433

(22) Filed: Oct. 30, 2002

(65) Prior Publication Data

US 2003/0117153 A1 Jun. 26, 2003

Related U.S. Application Data

(63) Continuation-in-part of application No. 10/150,903, filed on May 17, 2002.
(60) Provisional application No. 60/341,025, filed on Oct. 30, 2001, provisional application No. 60/341,022, filed on Oct. 30, 2001, provisional application No. 60/291,781, filed on May 17, 2001, provisional application No. 60/325,369, filed on Sep. 27, 2001, and provisional application No. 60/341, 022, filed on Oct. 30, 2001.

(51) Int. Cl.[7] .................. G01R 27/26; G01R 27/08; G01N 33/22
(52) U.S. Cl. .................. 324/663; 324/698; 324/685; 73/61.43
(58) Field of Search .................. 324/690, 664, 324/663, 667, 674, 681, 685, 694, 721, 698; 73/61.43, 61.41

(56) References Cited

U.S. PATENT DOCUMENTS

| 4,426,616 | A | * | 1/1984 | Maier ..................... 324/658 |
| 4,555,661 | A | | 11/1985 | Benson et al. |
| 4,915,084 | A | | 4/1990 | Gonze |
| 4,945,863 | A | | 8/1990 | Schmitz et al. |
| 4,971,015 | A | | 11/1990 | Gonze |
| 5,060,619 | A | | 10/1991 | Sakurai et al. |
| 5,089,703 | A | | 2/1992 | Schoen et al. |
| 5,103,184 | A | | 4/1992 | Kapsokavathis et al. |
| 5,119,671 | A | | 6/1992 | Kopera |
| 5,134,381 | A | * | 7/1992 | Schmitz et al. ............. 324/685 |
| 5,216,409 | A | | 6/1993 | Ament et al. |
| 5,230,322 | A | | 7/1993 | Curran et al. |
| 5,231,358 | A | | 7/1993 | Kapsokavathis et al. |
| 5,255,656 | A | | 10/1993 | Rader et al. |
| 5,301,542 | A | | 4/1994 | Meitzler et al. |
| 5,361,035 | A | | 11/1994 | Meitzler et al. |
| 5,367,264 | A | | 11/1994 | Brabetz |
| 5,416,425 | A | | 5/1995 | Mouaici |
| 5,503,004 | A | | 4/1996 | Agar |
| 5,594,163 | A | | 1/1997 | Suzuki |
| 5,612,622 | A | * | 3/1997 | Goldman et al. ............. 324/444 |
| 5,717,339 | A | | 2/1998 | Murphy et al. |
| 5,945,831 | A | | 8/1999 | Sargent et al. |
| 6,103,112 | A | * | 8/2000 | Sutton et al. ............. 210/198.2 |

FOREIGN PATENT DOCUMENTS

GB        2 210 459 A    6/1989

OTHER PUBLICATIONS

PCT International Search Report mailed Mar. 14, 2003.

* cited by examiner

Primary Examiner—Anjan K. Deb

(57) ABSTRACT

A sensor (40) includes a single capacitor (42) that operates in two different modes to obtain capacitance and conductance information when a mixture flows between the electrodes (44, 46) of the capacitor. The inventive sensor is particularly well-suited for making methanol content determinations within a mixture used to provide hydrogen to supply a fuel cell. Two different oscillators (180, 182) are selectively used to obtain the conductance and capacitance information. In a disclosed embodiment, a capacitor includes an outer electrode (44) that is received around an inner electrode (46) such that there is a spacing between the electrodes through which the mixture flows. The mixture acts as a dielectric of the capacitor allowing the conductance and capacitance measurements to be made. The example sensor includes a temperature sensor (76) conveniently supported within the inner electrode (46).

17 Claims, 5 Drawing Sheets

FUEL CELL MIXTURE SENSOR

CROSS REFERENCE TO RELATED APPLICATIONS

This application claims priority to U.S. Provisional Application Nos. 60/341,025 and 60/341,022, which were filed on 30 Oct. 2001. This application is a continuation-in-part of U.S. Ser. No. 10/150,903, which was filed on 17 May 2002, which claims priority to U.S. Provisional Application Nos. 60/291,781, which was filed on 17 May 2001; 60/325,369, which was filed on 27 Sep. 2001; and 60,341,022, which was filed on 30 Oct. 2001.

BACKGROUND OF THE INVENTION

1. Technical Field

This invention generally relates to fluid content sensors. More particularly, this invention relates to a sensor arrangement having a single capacitor that is used in two different modes to determine desired characteristics of a fluid mixture that is used to provide hydrogen to a fuel cell, for example.

2. Description of the Prior Art

A variety of sensors for determining fluid contents are known. Fuel sensors, for example, typically are used to determine the content of a fuel mixture within a fuel system of a vehicle. Some sensors are capable of determining the content of the fuel mixture such as a ratio or proportion of alcohol to gasoline within the fuel. Depending on the determined ratio, the ignition timing and fuel quantity supplied by fuel injectors may be adjusted by a suitable fuel flow control system.

It is known that the relative permittivity and conductivity of substances or fluids differ from each other because of the different oxygen levels within each, for example. Accordingly, the relative contents of a fluid mixture of known components may be a well-defined function of the fluid's relative permittivity, temperature and conductivity.

Known sensors take advantage of these known characteristics and utilize the electrical properties of the fluid mixture contents to make a determination regarding concentrations, for example. Sample patents in this field of endeavor that are directed toward fuel systems include U.S. Pat. Nos. 4,945,863 and 5,367,264. Each of these patents show approaches to providing a fuel sensor that utilizes the electrical properties of the fluid for making fuel content determinations.

While the current approaches have proven satisfactory, those skilled in the art are always striving to make improvements. For example, alternative power sources for vehicles, such as fuel cells, have particular measurement requirements. Additionally, packaging constraints on vehicle systems continuously cause an emphasis to be placed upon minimizing the size of components and maximizing the convenience of integrating them into vehicle systems. Additionally, cost savings are always a concern to automotive suppliers.

This invention addresses the need for providing an economical and convenient approach to measuring properties of a mixture used to provide fuel such as hydrogen to a fuel cell.

SUMMARY OF THE INVENTION

In general terms this invention is a sensor that utilizes a single capacitor operated in two different modes for determining the conductivity and permittivity of a mixture to provide information regarding the contents of the mixture.

In one example, the sensor has a generally cylindrical portion that is readily inserted into a selected location of a mixing chamber where several components are mixed to prepare a mixture for providing hydrogen to a fuel cell.

The capacitor of the sensor in one embodiment has a first, generally cylindrical electrode that is coaxially aligned with the other electrode. The mixture flows between the electrodes so that the appropriate conductivity and permittivity information can be determined. The capacitor effectively operates in two different modes (using two different oscillators in one example) so that the permittivity and conductivity measurements are made.

The sensor measurements can then be made available to another device that adjusts the supply of the components to the mixing chamber as necessary to achieve the desired contents of the mixture.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENTS

Figure 1:
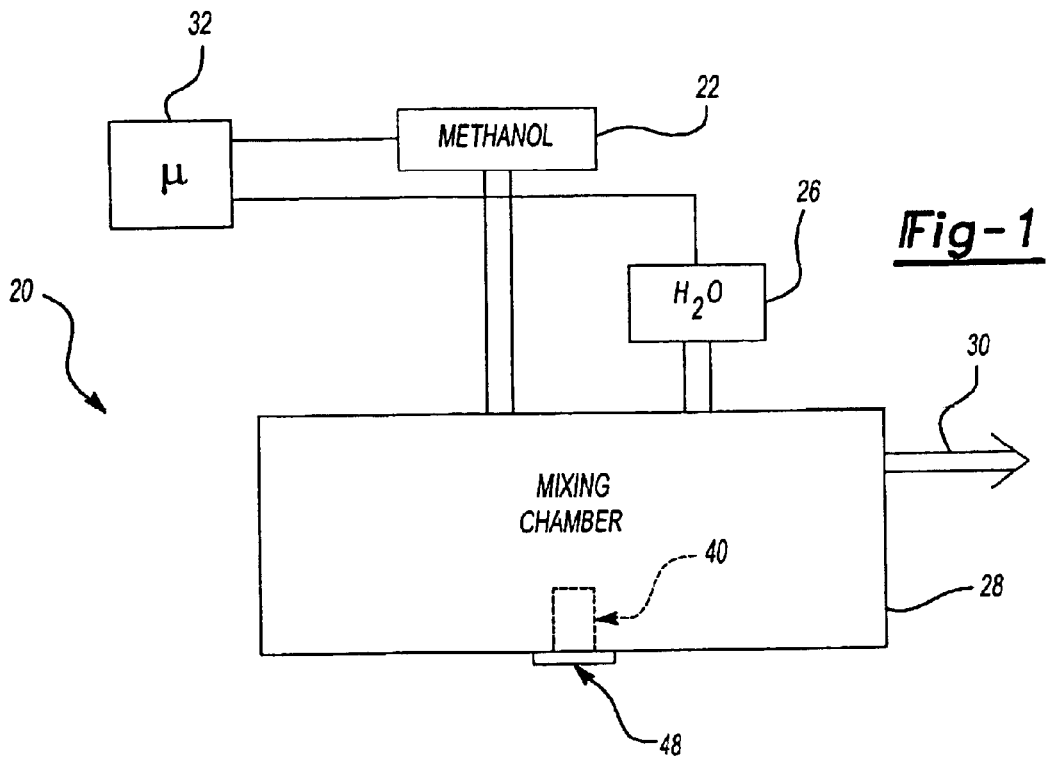
FIG. 1 schematically illustrates an example system incorporating a sensor designed according to this invention.

FIG. 1 schematically illustrates a system 20 for providing hydrogen to a fuel cell. In the illustrated arrangement, methanol 22 and water 26 are mixed within a mixing chamber 28. Hydrogen from the mixing chamber 28 is provided to a fuel cell (not illustrated) through an outlet 30.

A controller 32 controls the amount of each of the components supplied to the mixing chamber to achieve the desired percentages of methanol and water, for example, so that an appropriate reaction occurs to provide the desired amount of hydrogen for operating the fuel cell.

A sensor 40 is strategically placed at least partially within the mixing chamber 28 to provide the controller 32 information regarding the contents of the mixture within the mixing chamber 28. The sensor 40 designed according to this invention is a capacitive sensor that provides conductivity and permittivity information regarding the mixture within the mixing chamber 28. The sensor 40 preferably also provides temperature information to the controller 32. In at least one example, the controller 32 controls the amount of the various components supplied into the mixing chamber 28 responsive to information provided by the sensor 40.

Figure 2:
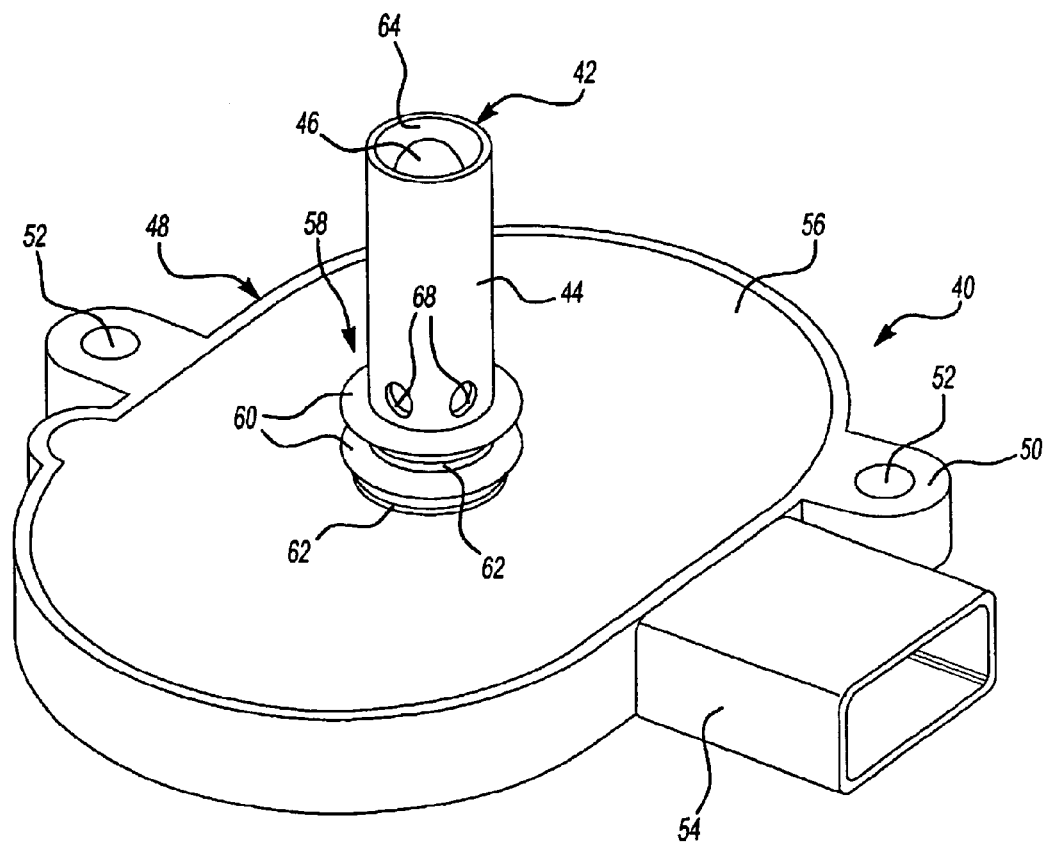
FIG. 2 schematically illustrates an example sensor designed according to this invention.
Figure 3:
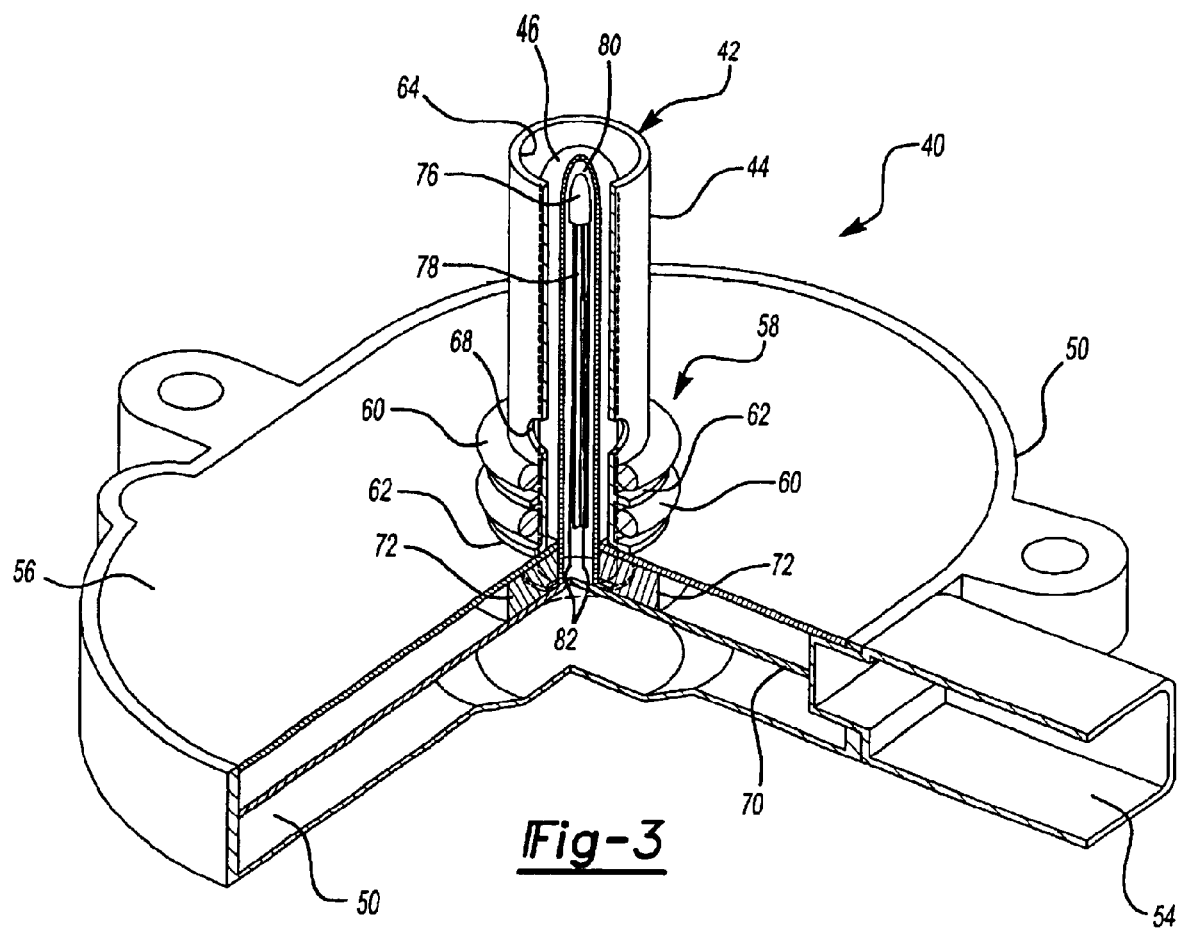
FIG. 3 is a partially cut-away, schematic illustration of selected components of the embodiment of FIG. 1.
Figure 4:
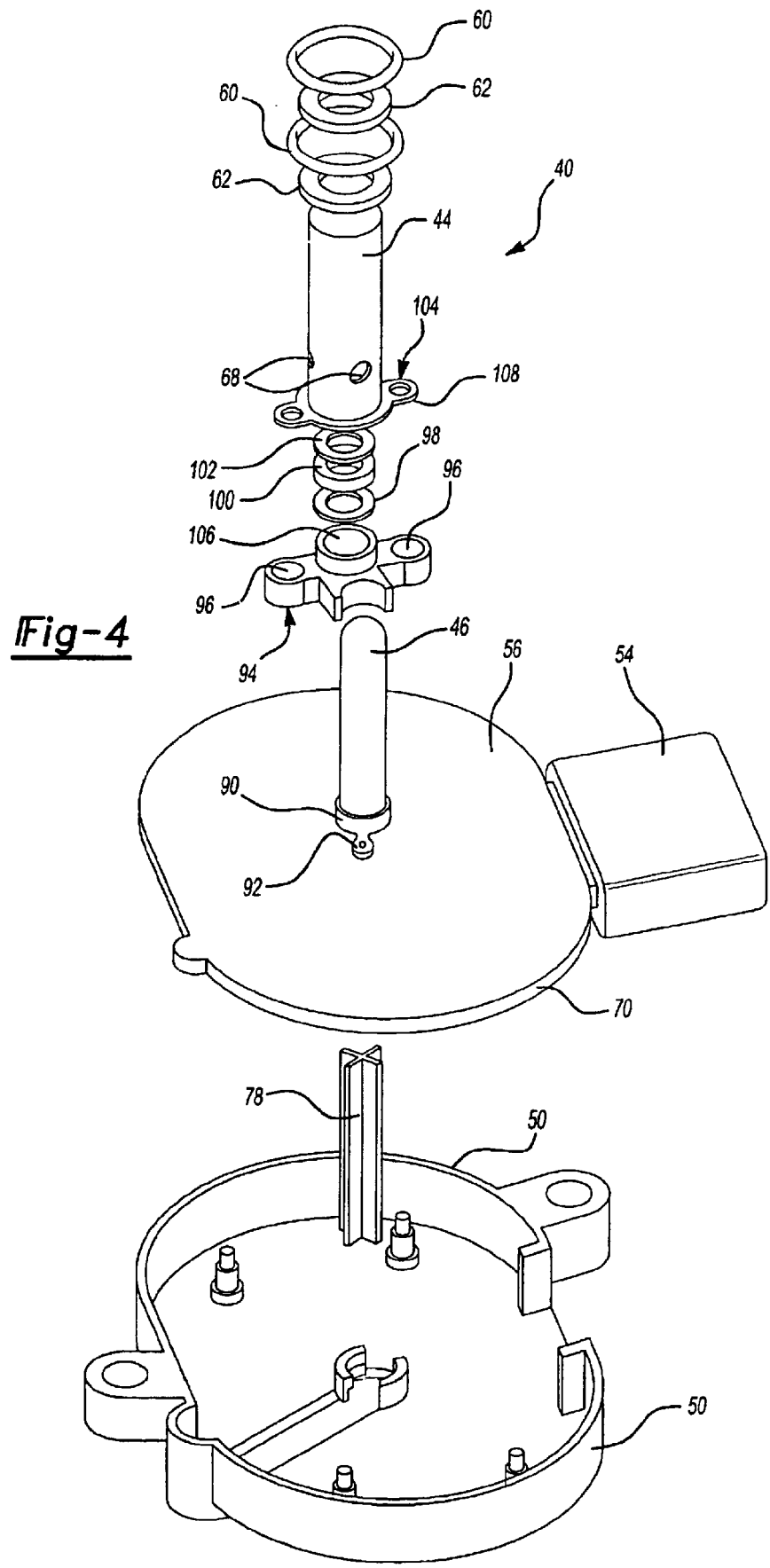
FIG. 4 is a schematic, exploded view of the embodiment of FIG. 2.

Referring to FIGS. 2 through 4, an example embodiment of a sensor designed according to this invention includes a capacitive sensor portion 42. A first electrode 44 is generally cylindrical and surrounds a second electrode 46. In the illustrated example, the first electrode 44 is the cathode and the second electrode 46 is the anode. As the mixture within the mixing chamber 28 flows between the electrodes 44 and 46, the capacitive measure provides information regarding the percentage of methanol and water, for example, within the mixture. The properties of methanol and water and their relationships to the output of a capacitive sensor are known. For example, the conductivity and permittivity information gathered by the sensor 40 provide an indication of the percentage of methanol within the mixture based upon the known properties of methanol (and the other components within the mixture). Those skilled in the art who have the benefit of this description will appreciate how to use such known properties with a sensor designed according to this invention to provide the information needed for their situation.

A sensor support portion 48 preferably is received against a corresponding portion of the mixing chamber 28. In the illustrated example, the sensor support portion 48 is adapted to remain outside of the mixing chamber. The sensor support portion 48 includes a housing 50 that has attachment portions 52 for securing the sensor in place relative to the mixing chamber 28. In the illustrated example, the attachment portions 52 comprise holes through which screws or other fasteners may be received for securing the sensor support portion 48 in place.

An electrical connector portion 54 extends away from the body 50 and facilitates making an electrical connection between the electronics of the sensor 40 (to be described below) and the controller 32. Conventional electrical connector configurations may be used to meet the needs of a particular situation.

A cover plate 56 cooperates with the housing portion 50 to enclose the electronics of the sensor 40. In the illustrated example, a sealing arrangement 58 is provided for preventing any fluid from leaving the mixing chamber 28 and protects the portions of the sensor that preferably do not get wet or exposed to other elements. Two O-rings 60 and two spacers 62 preferably are received about the exterior of the first electrode 44. The O-rings 60 seal off an opening in the mixing chamber through which the capacitor portion 42 is received. Each of the O-rings 60 preferably provides a sufficient seal on its own. Two O-rings preferably are used to provide a backup seal in the event that one of the O-rings should be damaged or otherwise fail.

The illustrated first electrode 44 has a generally cylindrical body that is open at both ends. An opening 64 is exposed to the mixture within the mixing chamber 28. A plurality of openings 68 preferably are provided in the sidewall of the body of the first electrode 44 so that the fluid within the mixing chamber 28 flows through the first electrode 44 and between the two electrodes 44 and 46 of the capacitor portion 42. In the illustrated example, the capacitor portion 42 preferably is generally vertical within the mixing chamber so that the fluid within the chamber flows downward through the opening 64 and out the openings 68. A variety of configurations may be used within the scope of this invention. Those skilled in the art will realize how to configure the electrodes of the capacitor portion 42 to best meet the needs of their particular situation.

The sensor support portion 48 preferably houses a printed circuit board 70 that supports electronics for operating the sensor. A spacer 72 maintains a desired distance between the plate portion 56 and the printed circuit board 70 and provides support for the first electrode 44 about the second electrode 46. The electronics (schematically illustrated in FIGS. 5 and 6) preferably provide the desired operation of the capacitor portion 42 to achieve the desired permittivity and conductivity measurements.

The inventive sensor assembly preferably also includes the ability to provide a temperature measurement of the fluid that serves as the dielectric of the capacitor portion 42. In the illustrated example, a temperature sensor 76, such as an NTC or thermistor device is supported within the second electrode 46. The body of the second electrode 46 preferably is hollow so that there is spacing between the temperature sensor 76 and the body of the electrode 46. In the illustrated example, a cross-shaped spacer 78 supports the temperature sensor 76 in the desired position within the second electrode 46.

The preferred arrangement includes a thermally conductive grease 80 that contacts the body of the electrode 46 and the temperature sensor 76 to ensure appropriate temperature conductivity to the sensor 76 to provide more accurate temperature readings. One example includes thermal grease to wet the surface of the electrode body and to couple it to the thermistor for maximum convective and radiative heat transfer to the thermistor device. It is preferred not to leave any spacing between the thermistor and the sensor body without thermal grease to avoid variable or extended response to a change in the mixture temperature.

Two leads 82 allow for making the appropriate electrical connections with the temperature sensor 76. The cross-shaped spacer 78 facilitates maintaining the desired spacing between the leads 82 within the second electrode 46 body. The leads 82 may be associated with appropriate electronics on the printed circuit board 70, for example. In another example, the controller 32 is directly coupled with the leads 82 through an appropriate connection made using the electrical connection portion 54.

As best appreciated from FIGS. 3 and 4, an example assembly process for making the example sensor device includes first assembling the printed circuit board 70 with the necessary electronics. The second electrode 46 preferably then is secured to the circuit board substrate and the appropriate electrical connections are made with the corresponding portions of the electronics on printed circuit board 70. The illustrated example includes a base portion 90 on the second electrode 46 that has two mounting holes 92 for receiving appropriate fasteners. Next, a base spacer 94 preferably is positioned over the second electrode 46. In the illustrated example mounting holes 96 are provided on the base spacer 94. Next, an O-ring 98 followed by a spacer 100 and another O-ring 102 preferably are received over the second electrode 46.

The first electrode 44 preferably is then received over the second electrode 46 until a base 104 of the first electrode 44 body is received over a boss 106 on the base spacer 94. The base 104 of the first electrode 44 preferably includes openings 108 that are aligned with the mounting holes 96 on the base spacer 94 so that screws or other fasteners may be inserted through each to secure the first electrode 44 in position.

The O-rings 102 and 98 establish a seal between the outer surface of the second electrode 46 and the inner surface of the outer electrode 44 so that any fluid entering between the electrodes does not leak through where it may potentially contact the electronics of the sensor assembly. The O-rings 98 and 102 and the spacer 100 also facilitate maintaining electrical isolation between the electrodes 44 and 46.

Next the printed circuit board 70 may be appropriately supported and secured in place within the housing portion 50 and the appropriate electrical connections made so that a suitable conductor can later be associated with the connector portion 54 to make a connection with the controller 32, for example. Next, the plate portion 56 preferably is received over the first electrode 44 and then secured to the housing portion 50. In one example, a heat staking operation is used for making this connection. The coupling between the plate portion 56 and the housing portion 50 preferably seals the assembly against fluid or other elements entering the housing 50.

The O-rings 60 and spacer 62 then may be positioned about the exterior of the first electrode 44. In this condition, the sensor 40 is prepared for appropriate insertion into the corresponding opening in the mixing chamber 28.

Attention will now be turned to the electronics used to operate the example embodiment of the inventive sensor. The general principles of making capacitance and conductance measurements are known. As will become apparent, the inventive sensor uses conventional measurement principles but also includes novel features distinguishing the inventive arrangement from prior sensors. The inventive sensor arrangement preferably provides information regarding the methanol content of the fluid mixture within the mixing chamber 28.

Figure 5:
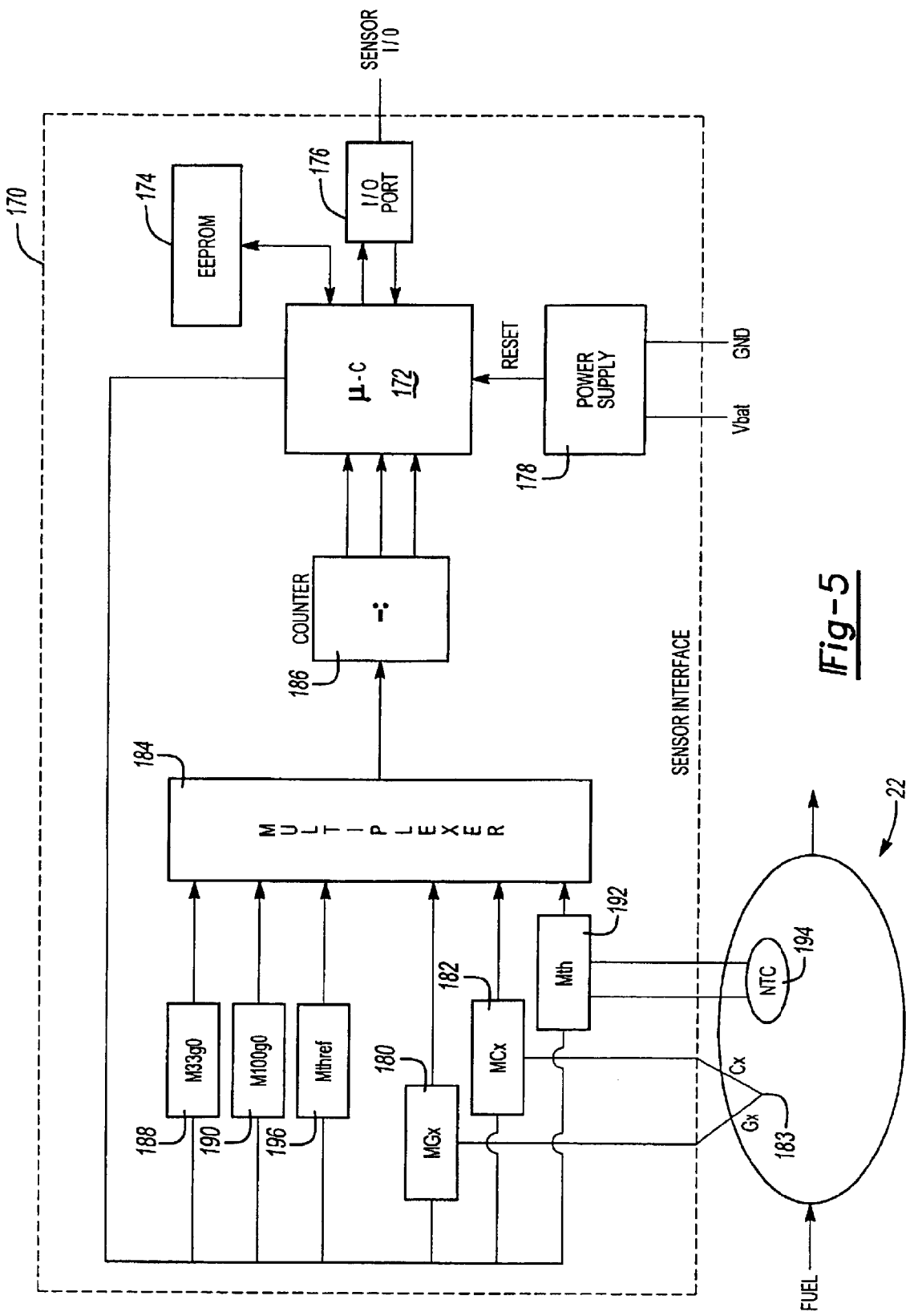
FIG. 5 schematically illustrates example electronics used to operate a sensor designed according to this invention.

FIG. 5 schematically illustrates the sensor capacitor 42 and electronics 170 for operating the sensor. A microprocessor 172 is suitably programmed to gather the capacity, temperature and conductivity information obtained by the sensor and to compare that information to data stored in the ROM of the controller 172 to make a mixture content determination. Calibration parameters of the sensor are stored in the EEPROM 174. In one example, the controller 172 ROM includes a look up table of a plurality of predetermined sensor values corresponding to specific known mixtures. The microprocessor 172 is programmed to utilize that information and provide an output through a conventional communication port 176 to be used by the mixture supply controller 32 that is responsible for the amount of methanol, water and air fed into the mixing chamber 28. A conventional power supply 178 powers the microprocessor 172.

One unique feature of this invention is the use of a single capacitor 42 to make the conductivity and permittivity measurements of the mixture. Two different oscillators 180 and 182 are selectively coupled with the capacitor 42 to make the two separate determinations (i.e., conductivity and capacity). The inventive arrangement includes a single mechanical connection 183 between the capacitor 42 and the oscillators 180 and 182. Instead of switching the connection to the capacitor 42, the example implementation of this invention includes switching the oscillator (180 and 182) outputs. In such a case parasitic capacitance does not influence the capacity to measure.

The electronics 170 include a multiplexer 184 that receives the output of the oscillators 180 and 182. In one example, one of the oscillators operates in a MegaHertz range while the other operates in a KiloHertz range. Because of these relatively high frequencies, a counter 186, which acts as a divider, is provided between the multiplexer 184 and the microprocessor 172 so that the microprocessor is capable of handling the signal information from the oscillators. Although schematically shown as separate "components," the various portions of FIGS. 5 or 6 may be implemented using a suitably programmed microprocessor, for example. The illustrated divisions are applicable to the described example but this invention is not so-limited.

The inventive arrangement includes operating the oscillators 180 and 182 at different frequencies and independent from each other so that the capacitor 42 is used in two different modes, depending on which oscillator is activated.

To compensate for component drifting and aging, reference oscillators 188 and 190 are provided. In one example, the reference oscillator 188 is set to provide an indication of a methanol content at a lower end of an expected spectrum. The oscillator 190 is set to provide an indication corresponding to a methanol content at an opposite end of an expected spectrum. In one example the reference capacitor 188 corresponds to a ten percent methanol content while the reference capacitor 190 corresponds to a ninety percent methanol content. The reference oscillators preferably are selected to remain fixed so that they are not affected over the lifetime of the sensor assembly.

As mentioned, another factor used when making a mixture content determination is the temperature of the mixture. The illustrated example arrangement includes another oscillator 192 that is coupled with the thermistor 80 that obtains mixture temperature information. A reference oscillator 196 is chosen to provide calibration information to compensate for drift or aging of the oscillator 192 over time.

The use of oscillators in combination with capacitors for obtaining the necessary information regarding the mixture content are known. One advantageous difference of this invention is that a single capacitor 42 is used in two modes and only a single mechanical connection 183 between the capacitor 42 and the oscillators 180 and 182 simplifies the overall assembly and makes it more economical.

The microprocessor 172 preferably is programmed to selectively switch between the oscillators 180 and 182 to make the appropriate conductivity or capacity measurements. The example of FIG. 6 includes electronic switches 200 and 202 that are selectively operated by the microprocessor 172 to achieve the desired oscillator operation to obtain the desired measurement. Similarly, the microprocessor 172 controls electronic switches 204 and 206 to select either of the reference oscillators 188 and 190.

Figure 6:
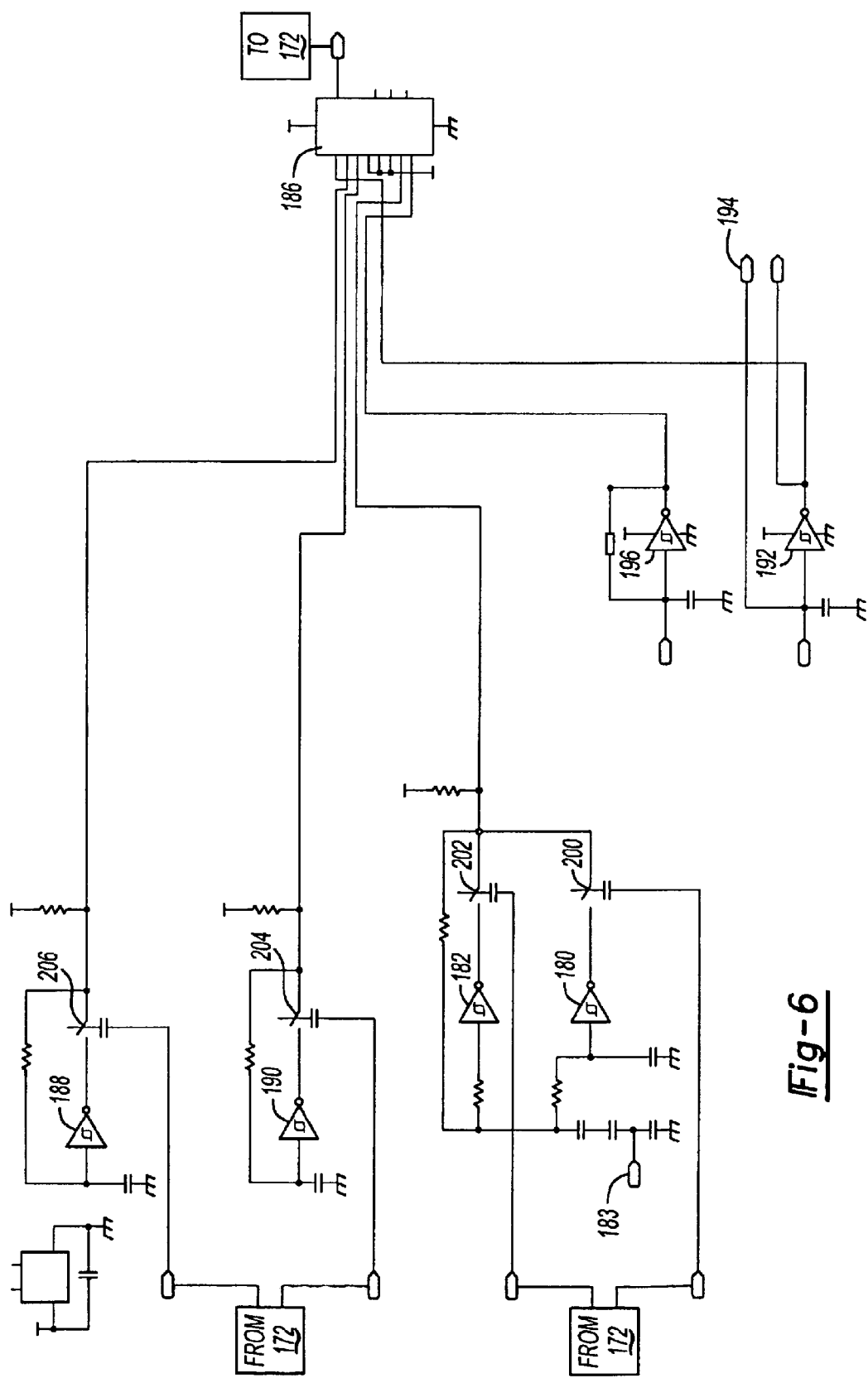
FIG. 6 schematically illustrates, in somewhat more detail, an example implementation of electronics for operating a sensor designed according to this invention.

The arrangement of electronics for operating a sensor designed according to this invention can take a variety of forms. The example of FIG. 6 is one particular implementation of the overall inventive strategy. Those skilled in the art who have the benefit of this description will be able to select from commercially available electronic components or to specially design hardware and software to meet the needs of their particular situation.

Figure 7:
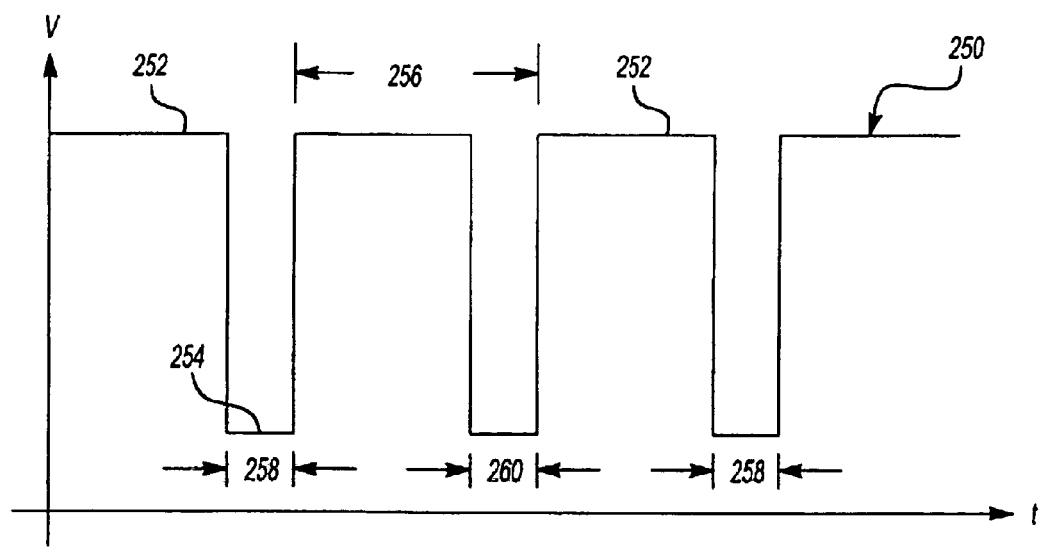
FIG. 7 graphically illustrates an example sensor output in an arrangement designed according to this invention.

In one example, the output from the sensor 40 is a frequency and negative pulse width modulated signal. FIG. 7 graphically illustrates one particular output strategy that is usable with a sensor designed according to this invention. The sensor output signal 250 includes a series of positive pulses 252 and negative pulses 254. In this example, the frequency 256 of the pulse train provides an indication of the percentage of methanol within the mixture. For example, a 50 Hertz frequency corresponds to a zero percent methanol content. A 150 Hertz frequency corresponds to a 100 percent methanol content. Every ten Hertz increment between 50 Hertz and 150 Hertz corresponds to a ten percent change in the amount of methanol present within the mixture. Depending on the chosen configuration of the microprocessor 172, either the controller 32 or the microprocessor 172 is programmed to recognize the methanol content information based upon the frequency of the sensor output signal 250.

The inventive arrangement also includes altering the duty cycle (i.e., the relative positive pulse and negative pulse widths) to provide an indication of the detected temperature and the detected conductivity, respectively. In the illustrated example, every other negative pulse width is indicative of temperature or conductivity. The pulse width 258 provides an indication of the temperature detected by the temperature sensor 76. In one example, a one millisecond pulse width corresponds to 0° C. while a five millisecond pulse width 258 corresponds to a 100° C. measurement. Either the microprocessor 172 or the controller 32 is programmed to correlate the pulse width 258 timing information with a preselected temperature scale.

Every alternate negative pulse has a pulse width 260 that provides an indication of the conductivity information gathered by the capacitor portion 42 of the sensor 40. An appropriate scale relating the timing information (i.e., the pulse width 260) to conductivity measurements preferably are selected to meet the needs of a given situation. Those skilled in the art who have the benefit of this description will realize what will work best for their particular situation.

By utilizing every other negative pulse width as providing information regarding the measured temperature and conductivity, respectively, the inventive arrangement provides a unique sensor output that conveniently and economically conveys the measured information along with the measured permittivity information (i.e., percentage methanol content). Of course, a variety of sensor output formats are within the scope of this invention.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A sensor useful for measuring a property of a mixture, comprising:
   a capacitor having a first, generally cylindrical electrode and a second electrode at least partially surrounded by the first electrode, the electrodes being spaced apart such that the mixture flows between the electrodes;
   a first oscillator that causes the capacitor to operate in a first mode to provide an indication of the capacitance of the capacitor when the mixture is between the electrodes;
   a second oscillator that causes the capacitor to operate in a second mode to provide an indication of the conductance of the capacitor when the mixture is between the electrodes;
   a controller that switches between the first and second oscillators to obtain the respective indications; and
   a temperature sensor supported within the second electrode, the sensor providing an indication of the mixture temperature.

2. The sensor of claim 1, wherein the controller uses the temperature information, the capacitance indication and the conductance indication to determine the property of the mixture.

3. The sensor of claim 2, including a memory portion having a plurality of predetermined values indicative of mixture properties and wherein the controller determines the property from among the predetermined values based upon the temperature information, the capacitance indication and the conductance indication.

4. The sensor of claim 1, wherein the second electrode is hollow and including a spacer that supports the temperature sensor in a chosen position within the second electrode.

5. The sensor of claim 1, including a thermally conductive grease in a spacing between an inner surface of the second electrode and the temperature sensor and wherein the thermally conductive grease contacts the second electrode and the temperature sensor.

6. A sensor useful for measuring a property of a mixture, comprising:
   a capacitor having a first, generally cylindrical electrode and a second electrode at least partially surrounded by the first electrode, the electrodes being spaced apart such that the mixture flows between the electrodes;
   a first oscillator that causes the capacitor to operate in a first mode to provide an indication of the capacitance of the capacitor when the mixture is between the electrodes;
   a second oscillator that causes the capacitor to operate in a second mode to provide an indication of the conductance of the capacitor when the mixture is between the electrodes; and
   a controller that switches between the first and second oscillators to obtain the respective indications, wherein the sensor provides an output wave form that has a period corresponding to the capacitance indication and timing information corresponding to the conductance indication.

7. The sensor of claim 6, including a single mechanical connection between the first and second oscillators and the capacitor, the controller selectively electrically operating the respective oscillators with the capacitor to obtain a desired one of the indications.

8. The sensor of claim 7, including electronic switches associated with each of the oscillators that are responsive to the controller to electrically operate the selected oscillator with the capacitor.

9. The sensor of claim 6, wherein the timing information comprises a pulse width.

10. The sensor of claim 6, wherein the timing information comprises a duty cycle.

11. The sensor of claim 6, wherein the sensor output includes second timing information corresponding to a temperature indication obtained by a temperature sensor included in the sensor.

12. The sensor of claim 11, wherein the timing information corresponding to the conductance indication and the second timing information corresponding to the temperature indication are provided in alternating cycles of the wave form output.

13. A sensor useful for measuring a property of a mixture, comprising:
   a capacitor having a first, generally cylindrical electrode and a second electrode at least partially surrounded by the first electrode, the electrodes being spaced apart such that the mixture flows between the electrodes, wherein the first electrode comprises a hollow, generally cylindrical body with open ends and the second electrode comprises a generally cylindrical body having at least one end that is closed and including a sealing arrangement near one end of the electrodes completely surrounding the second electrode body and contacting a corresponding portion of an inside of the first electrode body to establish a fluid-tight seal between the first and second electrodes near the one end;

a first oscillator that causes the capacitor to operate in a first mode to provide an indication of the capacitance of the capacitor when the mixture is between the electrodes;

a second oscillator that causes the capacitor to operate in a second mode to provide an indication of the conductance of the capacitor when the mixture is between the electrodes; and a controller that switches between the first and second oscillators to obtain the respective indications.

14. The sensor of claim 13, wherein the first electrode includes at least one opening in a sidewall of the electrode to allow fluid flow through one of the open ends of the first electrode, between the two electrodes and through the sidewall opening.

15. The sensor of claim 13, including a sensor support portion that houses the controller and the oscillators such that the controller and the oscillators are fluidly isolated from the mixture that flows between the electrodes.

16. A method of determining a methanol content of a mixture, comprising the steps of:

providing a single capacitor having two electrodes between which the mixture flows;

using the capacitor in a first mode to obtain an indication of the conductance of the capacitor with the mixture between the electrodes;

using the capacitor in a second mode to obtain an indication of the capacitance of the capacitor with the mixture between the electrodes;

determining a temperature of the mixture; determining the methanol content of the mixture, using the determined temperature, the capacitance indication and the conductance indication; and providing a wave form sensor output that has a period corresponding to the capacitance indication, a first pulse width corresponding to the determined temperature and a second pulse width corresponding to the conductance indication.

17. The method of claim 16, including electrically operating a first oscillator having a first frequency associated with the capacitor in the first mode and electrically operating a second oscillator having a second frequency associated with the capacitor in the second mode.

* * * * *